(12) United States Patent
D'Aversa et al.

(10) Patent No.: US 6,712,838 B2
(45) Date of Patent: Mar. 30, 2004

(54) BRAIDED SUTURE WITH IMPROVED KNOT STRENGTH AND PROCESS TO PRODUCE SAME

(75) Inventors: Margaret D'Aversa, Whitehouse Station, NJ (US); Howard L. Scalzo, Jr., Kenilworth, NJ (US); Dennis D. Jamiolkowski, Long Valley, NJ (US); Rao S. Bezwada, Whitehouse Station, NJ (US); Donald G. Hill, Hopatcong, NJ (US); Alastair W. Hunter, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/801,035

(22) Filed: Mar. 7, 2001

(65) Prior Publication Data

US 2001/0018599 A1 Aug. 30, 2001

Related U.S. Application Data

(62) Division of application No. 09/159,025, filed on Sep. 23, 1998, now abandoned.
(60) Provisional application No. 60/061,721, filed on Oct. 10, 1997.

(51) Int. Cl.[7] ............................ A61L 17/00; A61B 17/04
(52) U.S. Cl. ........................................ 606/230; 427/2.31
(58) Field of Search .................................. 606/228, 229, 606/230, 231; 427/2.31

(56) References Cited

U.S. PATENT DOCUMENTS

| | | | |
|---|---|---|---|
| 3,257,702 A | 6/1966 | Kurtz | 28/72 |
| 3,636,956 A | 1/1972 | Schneider | 128/335.5 |
| 3,791,388 A | 2/1974 | Hunter et al. | 128/335.5 |
| 3,839,524 A | 10/1974 | Adams et al. | 264/131 |
| 4,027,676 A | 6/1977 | Mattei | 128/335.5 |
| 4,201,216 A | 5/1980 | Mattei | 128/335.5 |
| 4,470,941 A | 9/1984 | Kurtz | 264/136 |
| 4,595,713 A | 6/1986 | St. John | 523/105 |
| 4,705,820 A | * 11/1987 | Wang et al. | 524/381 |
| 4,788,979 A | 12/1988 | Jarrett et al. | 128/335.5 |
| 4,791,929 A | 12/1988 | Jarrett et al. | 128/335.5 |
| 4,994,074 A | 2/1991 | Bezwada et al. | 606/230 |
| 5,178,629 A | 1/1993 | Kammerer | 606/224 |
| 5,304,205 A | 4/1994 | Shinoda et al. | 606/230 |
| 5,442,032 A | 8/1995 | Arnold et al. | 528/354 |
| 5,522,842 A | * 6/1996 | Shalaby | 606/230 |
| 5,609,609 A | 3/1997 | Ohshima et al. | 606/231 |
| 5,618,314 A | 4/1997 | Harwin et al. | 606/232 |
| 5,817,129 A | 10/1998 | Labrecque et al. | 606/228 |

FOREIGN PATENT DOCUMENTS

| | | | |
|---|---|---|---|
| EP | 0 441 537 | 8/1991 | C08G/63/08 |
| EP | 0 839 542 A2 | 5/1998 | A61L/17/00 |
| WO | WO 86/00020 A1 | 1/1986 | |

* cited by examiner

Primary Examiner—Cary E. O'Connor

(57) ABSTRACT

The present invention discloses a process for producing a braided suture having an improved knot strength comprising heating a braided suture coated with a low molecular weight biocompatible polymer to a temperature sufficient to melt the low molecular weight biocompatible polymer for a time sufficient to allow the low molecular polymer to be redistributed into the interstices of the braided suture thereby providing a coated braided suture with an improved knot tensile strength. Also disclosed is the coated braided suture having a low molecular weight polymer optimally dispersed throughout the braided suture's cross-section.

11 Claims, 1 Drawing Sheet

SIMPLE KNOT

SIMPLE KNOT
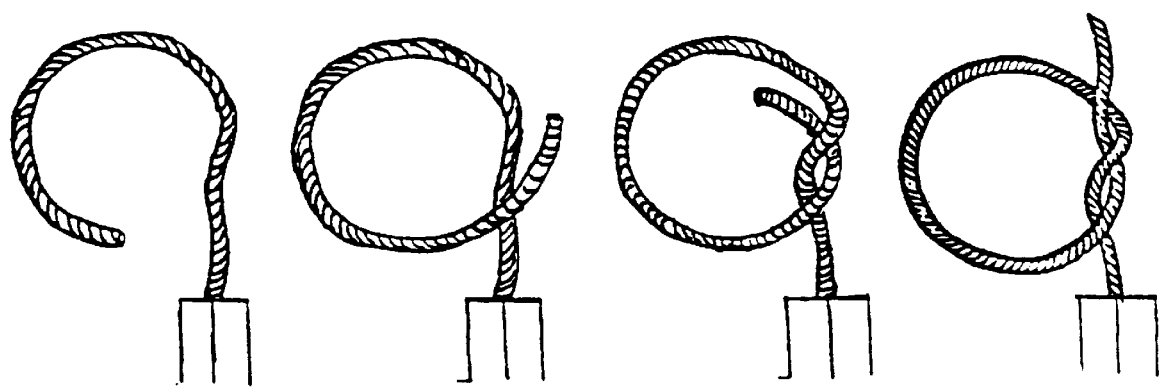

BRAIDED SUTURE WITH IMPROVED KNOT STRENGTH AND PROCESS TO PRODUCE SAME

This application is a divisional application of U.S. Ser. No. 09/159,025, filed Sep. 23, 1998, now abandoned, which claims the benefit of U.S. Ser. No. 60/061,721, filed Oct. 10, 1997.

FIELD OF THE INVENTION

This invention generally relates to a braided suture and a process for producing a braided suture. More specifically the present invention discloses a process for producing a braided suture with improved knot strength.

BACKGROUND OF THE INVENTION

Braided multifilament sutures are commonly used in surgery because of their excellent flexibility and handling properties. Braided sutures are generally used because an equivalent monofilament suture of the same material would be too stiff to be used as a suture. However, braiding creates inherent limitations in the properties of the final suture. For example braided sutures generally have rougher surfaces and may have lower overall straight and knot tensile strengths as compared to a monofilament suture of the same size. To improve the surface characteristics of braided sutures the surface of these sutures are generally coated with a lubricant to avoid the undesirable side effects of suture roughness (i.e. excessive tissue abrasion as the suture is passed through tissue) and difficulty in sliding down knots as the surgeon secures the suture in place. Suture coatings can be applied by a variety of methods. It is typical however, that they are applied by drip coating or dip coating the suture with a film-forming polymer suspended in or dispersed in a volatile solvent. The coated suture is then dried by passing the suture through a drying oven. Although coating the braided suture solves many of the issues associated with surface roughness it does not address how to improve the tensile strengths of braided sutures, particularly the knot tensile strength.

To overcome the limitations imposed by braided sutures Hunter and Rosen proposed in U.S. Pat. No. 3,791,388 to construct a multifilament yarn impregnated with an adhesive binder covered with a ribbon like helical winding. The Hunter-Rosen suture had a higher knot strength compared to conventional coated braided sutures. Unfortunately little further research has been done to develop braided sutures with improved knot strengths.

It is an object of the present invention to provide a process for producing a braided multifilament suture with an improved knot strength. A further object of the present invention is to provide a braided suture with an improved knot strength.

SUMMARY OF THE INVENTION

We have discovered a process for producing a braided suture having an improved knot strength comprising heating a braided suture coated with a biocompatible polymer to a temperature sufficient to melt the biocompatible polymer for a time sufficient to allow the polymer to be redistributed into the interstices of the braided suture thereby providing a coated braided suture with an improved knot tensile strength.

In a further embodiment of the present invention we have also discovered a coated braided suture with an improved knot strength comprising a braided suture having a biocompatible polymer dispersed throughout the braided suture.

These and other objects and advantages of the present invention will be apparent to one of skill in the art from the following Drawings, Detailed Description, Examples and claims.

BRIEF DESCRIPTION OF THE DRAWING

The FIGURE illustrates the knot used to test the knot strength of the improved suture.

DETAILED DESCRIPTION OF THE INVENTION

We have discovered that by optimizing the distribution of a biocompatible polymer (preferably of low molecular weight) in a braided suture that the suture's knot strength can be improved (while maintaining suture flexibility) as compared to conventionally coated sutures. Low molecular weight biocompatible polymers have been used to coat and lubricate the external surfaces of braided sutures for many years. Although lubricating the external surface of a suture may significantly impact the performance of a braided suture by making it easier to pass through tissue and tie knots, no one previously appreciated that controlling the distribution of the coating polymers throughout the braided suture's cross-section would impact suture performance. We, however, have discovered that significant improvements in the knot tensile strength of braided sutures could be achieved by redistributing the coating into the interior of the braided suture.

Suitable polymers for use in the present invention are well known. By far, the most widely used polymers for medical applications are aliphatic polyesters, however, polyoxalates and polyoxaesters are also well suited for use in the present invention. Suitable biocompatible polymers for coating applications, include but are not limited to, those described in U.S. Pat. Nos. 3,942,532; 4,624,256; 4,788,979; 4,791,929; 4,994,074; 5,007,923; 5,019,094; 5,037,950; 5,047,048; 5,076,807; 5,133,739; 5,442,016; 5,464,929; 5,618,552; 5,597,579; 5,648,088; and 5,607,687, all hereby incorporated by reference herein.

Lactone monomers have been described in the art, for example in Polymer, 1979, Vol. 20, 1459–1464 by Gilding and Reed. Examples of lactone monomers include monomers selected from the group consisting of glycolide (or glycolic acid) lactide, (D, L, meso and D, L blends and lactic acid) 1,4-dioxanone, trimethylene carbonate, δ-valerolactone, ε-caprolactone, 1,4-dioxepan-2-one, 1,5-dioxepan-2-one, alkyl substituted derivatives of these compounds, cyclic dimers of these compounds and combinations of two or more thereof. The preferred lactone monomers are ε-caprolactone, 1,4-dioxanone, 1,4-dioxepan-2-one, 1,5-dioxepan-2-one, trimethylene carbonate, glycolide and lactide. The most preferred lactone monomers are ε-caprolactone, 1,4-dioxanone and glycolide. For the purpose of describing this invention, an "ether lactone" is 1,4-dioxepan-2-one, 1,5-dioxepan-2-one, and substituted equivalents of these compounds as well as the cyclic dimers of these compounds.

Many biocompatible bioabsorbable aliphatic polyesters that are solids at room temperature, may be used as the coating material in the present invention. Suitable bioabsorbable polymers include solid homopolymers poly(p-dioxanone), and copolymers of ε-caprolactone and trimethylene carbonate. Copolymers of ε-caprolactone should be composed of from about 99 mole percent to about 70 mole percent and preferably from 95 mole percent to 85 mole percent of ε-caprolactone repeating units with the remainder of the polymer being a plurality of second lactone repeating units. The second lactone repeating units will be selected from the group consisting of glycolide repeating units, lactide repeating units, 1,4-dioxanone repeating units (including alkyl derivatives thereof i.e. 6,6-dimethyl-1,4-dioxan-2-one such as are described in European Patent Application No. 97301725.4), 1,4-dioxepan-2-one repeating units, 1,5-dioxepan-2-one repeating units, trimethylene carbonate repeating units (including alkyl substituted derivatives thereof such as are described in U.S. Pat. No. 5,412,068 incorporated herein by reference), and combinations thereof. Preferred are copolymers of ε-caprolactone that are semi-crystalline solids at room temperature. The solid polymers of trimethylene carbonate should be composed of from in the range of from about 1 to about 20 mole percent or from about 100 to about 80 mole percent of trimethylene carbonate with the remainder of the copolymer being composed of a plurality of repeating units selected from the group consisting of glycolide repeating units, lactide repeating units, p-dioxanone repeating units, ε-caprolactone repeating units, and combinations thereof. It is preferred for the trimethylene carbonate copolymers to have crystalline regions formed by the second repeating units wherein the crystalline regions provide at least 5 percent crystallinity to the final copolymer. The solid polymers may be linear, branched, or star branched; block copolymers or terpolymers; segmented block copolymers or terpolymers. These polymers will also be purified to substantially remove unreacted monomers which may cause an inflammatory reaction in tissue.

The preferred aliphatic polyesters for use as coatings are low molecular weight copolymers selected from the group consisting of poly(ε-caprolactone-coglycolide), poly(ε-caprolactone-co-trimethylene carbonate), poly(ε-caprolactone-co-lactide), and poly(ε-caprolactone-co-p-dioxanone). The mole percent of ε-caprolactone repeating units in these polymers should be in the range of from 100 to about 80 mole percent and preferably in the range of from 95 to 85 mole percent. Most preferably these polymers will be statistically random copolymers.

The polymeric coating of this invention can be a random, block or segmented polymer. Preferably, if the suture is absorbable the coating polymer is an absorbable polymer. A polymer is "absorbable" within the meaning of this invention if it is capable of breaking down into small, non-toxic segments which can be metabolized or eliminated from the body without harm. Generally, absorbable polymers, hydrolyze, and degrade upon exposure to bodily tissue, resulting in a significant weight loss.

The hydrolysis reaction may be enzymatically catalyzed in some cases. Complete bioabsorption, i.e. complete weight loss, may take some time, although preferably complete bioabsorption occurs within twelve months, most preferably within six months.

The preferred random copolymers can be made using conventional polymerization techniques. The reactive components can be charged to a suitable polymerization vessel, and subjected to an elevated temperature for a sufficient period of time to form the polymer of desired molecular weight and thus the desired viscosity. These polymers may be formed in a ring opening polymerization reaction. Currently, it is preferred to initiate the ring opening polymerization with high boiling alcohols (such as 1-dodecanol), diols and triols (such as 1,2-propanediol, 1,3-propanediol, diethylene glycol, or glycerol) or polyols (such as polyethyleneglycols, polypropyleneglycols and polyethylenepropyleneglycols). Additionally, some of the monomers described above may be replaced by an equivalent amount of the corresponding acid (such as the substitution of two equivalents of glycolic acid for glycolide or two equivalents of L-lactic acid for L-lactide).

The preferred random copolymers exhibit an inherent viscosity, as measured in a 0.1 gram per deciliter (g/dL) of hexafluoroisopropanol (HFIP) at 25° C., between about 0.05 to about 0.8 dL/g, preferably about 0.10 to about 0.60 dL/g. If the inherent viscosity were less than about 0.05 dL/g, then the polymer may not have the integrity necessary for the preparation of films or coatings for the surfaces of various surgical and medical articles.

On the other hand, although it is possible to use polymers with an inherent viscosity greater than about 0.8 dL/g, it may be exceedingly difficult to do so.

The polymer may be applied as a coating using conventional techniques. For example, the polymer may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed. The drying process is usually accomplished by heating for 10 minutes or less.

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 10 parts by weight based on the total weight equaling 100 parts. If the amount of coating on the suture were too great, then it may increase the risk that the coating may flake off when the suture is passed through tissue.

After the suture is coated, as part of the drying process or in a subsequent processing step, the coating polymer is heated to a sufficient temperature for a sufficient time to soften the coating polymer and allow the coating polymer to be mobilized and penetrate the interstices of the braided suture. Because the coating must be heated to its softening temperature, it will be readily apparent to one skilled in the art that the polymer used in the underlying braid filament should have a higher melting temperature than the coating polymer's softening point or the filaments in the braid may melt or loose their molecular orientation (i.e. the straight tensile strength of the filaments will be reduced). Therefore, an appropriate choice of braided suture material and coating material should be made. However, because the relationship between polymer composition, molecular weight and softening point is well established in the art those skilled in the art should not be significantly limited by these concerns.

The temperature that the low molecular weight polymer may be heated to should be at least its softening temperature, however, temperatures in excess of its softening temperature may be utilized as long as the temperature and exposure time do not adversely affect the underlying braid filaments to unacceptable levels or result in the low molecular weight polymer dripping off the suture. In many cases the temperature of the heat treatment will be above the softening temperature of the low molecular weight biocompatible polymer and less than 100° C. above the softening point of the polymer. As a general guideline, but in no way limiting the scope of this invention, it is preferred that the heat treating temperature will be above 60° C., more preferably above 80° C. and below 100° C. above the softening point of the low molecular weight biocompatible polymer and preferably 50° C. above the softening point of the low molecular weight biocompatible polymer. In the case of polymeric coatings that are non-crystalline in nature, there will be no melting, thus the elevated temperature is needed only to reduce the viscosity of the coating to allow for redistribution from the surface of the suture.

The coating should generally be heated for a time sufficient to allow the coating to redistribute, the amount of time will of course depend on the temperature, viscosity of the coating polymer and the braid construction. However, by way of a general guideline the coating polymer should be heated to at least its softening point and preferably less than 100° C. above its softening point temperature for at least about 20 minutes, preferably about 30 minutes to about 72 hours, more preferably about 1 hour to about 72 hours, and most preferably about 5 hours to about 20 hours.

The low molecular weight coating polymers may be used with braided sutures made from a variety of synthetic absorbable polymers such as homopolymers and copolymers of glycolide, lactide (which includes L-, D-, and meso-forms of lactide and mixtures thereof), ε-caprolactone, p-dioxanone, trimethylene carbonate, 1,4-dioxepan-2-one, poly(alkylene oxalate), polyoxaesters and mixtures of such polymers with each other and with other compatible absorbable compositions as those described; for example, in U.S. Pat. Nos. 3,636,952 and 2,683,136 which patents are herewith incorporated herein by reference. One suitable suture composition would include copolymers of p-dioxanone, trimethylene carbonate and glycolide and copolymers of lactide and p-dioxanone. Preferred are suture compositions derived from lactide and glycolide sometimes referred to herein as simply homopolymers and copolymers of lactide and glycolide and copolymers of glycolide and ε-caprolactone, most preferred are 95/5 mole percent copolymers of poly(lactide-co-glycolide) and 90/10 mole percent copolymers of poly(lactide-co-glycolide).

Suitable nonabsorbable sutures include cotton, linen, silk (although silk is referred to as a nonabsorbable material it is broken down in the human body), nylon, polyethylene terephthalate and polyolefins (i.e. polypropylene which includes isotactic and syndiotactic polypropylene and blends thereof, as well as, blends composed predominantly of isotactic or syndiotactic polypropylene blended with heterotactic polypropylene and polyethylene (such as is described in U.S. Pat. No. 4,557,264 issued Dec. 10, 1985 assigned to Ethicon, Inc. hereby incorporated by reference) and copolymers composed predominantly of propylene and other alpha-olefins such as ethylene (which is described in U.S. Pat. No. 4,520,822 issued Jun. 4, 1985 assigned to Ethicon, hereby incorporated by reference).

Appropriate techniques for braiding sutures are well known in the art. Suitable techniques for braiding sutures may be found in one or more of the following U.S. Pat. Nos. 5,662,682; 5,456697; 5,306,289; 5,261,886; 5,181,923; 5,133,738; 5,059,213 and 5,019,093 which are hereby incorporated by reference herein.

The braided suture after being coated and heat treated to redistribute the low molecular weight polymer within the suture. The coating polymer generally resides on the outer surface of the suture. Although we do not wish to be limited by scientific theory we believe that the heat treatment after coating causes the low molecular weight polymeric coating to wick into and around a greater number of filaments making up the braid construction and is more evenly distributed around the individual filaments. This enables the individual filaments to slip over one another when tied in a knot thereby more evenly distributing the load between filaments.

The braided sutures produced by the present invention can be used in numerous surgical procedures. One preferred suture applications for braided 95/5 poly(lactide-co-glycolide) sutures with a coating of 90/10 poly(ε-caprolactone-co-glycolide) is to utilize these sutures in orthopedic applications. For example this suture may be used with suture anchors and screws such as those described in U.S. Pat. Nos. 4,898,156; 4,899,743; 4,946,468; 4,968,315; 5,116,337; 5,192,303; 5,217,486; 5,306,280; 5,356,413; 5,372,599; 5,411,523; 5,417,712; 5,441,502; 5,486,197; 5,522,845; 5,545,180; and 5,618,314 (all hereby incorporated by reference herein).

The following examples illustrate the preferred embodiments of this invention, and should not be interpreted to limit the scope of the claimed invention.

EXAMPLE 1

Process Description of Manufacturing Suture

The following is a description of the processing of a Size 2 suture of Polyglactin 095 Polymer(PG-095 Polymer, 95 mole percent L(-)lactide/5 mole percent glycolide). The comonomers were polymerized and the resulting resin extruded into filaments that were oriented, braided into a suture and coated.

Polymerization:

The chemical reaction for the synthesis of PG-095 polymer consists of reacting a mixture comprised of 95 mole percent of L(−)lactide and 5 mole percent of glycolide monomer with a molecular weight control agent, dodecanol, in the presence of a catalyst (stannous octoate catalyst solution, 0.331 molar in toluene). The amount or quantity of dodecanol added to a reaction is dependent upon the desired final inherent viscosity (molecular weight). The inherent viscosity of this polymer was 1.61 dl/g as measured in hexafluoroisopropanol (HFIP) at 25° C. at a concentration of 0.1 g/dl. The PG-095 polymer was prepared in a 60 kg batch size in a 15 gallon reactor.

The polymer was prepared by charging all ingredients including the catalyst solution to a reactor equipped with a vacuum and a nitrogen source. The contents of the reactor were placed under vacuum to remove the solvent used in the preparation of the catalyst and any ambient moisture that may have entered the reactor during the charging process. The reactor vacuum was released with nitrogen. The vacuum/nitrogen step was repeated at least once more. The content of the reactor were then heated under nitrogen atmosphere to temperatures in the range of 180–195° C. for one and one half hours.

The divided polymer was vacuum dried. This was done at a pressure of 0.5 mm of mercury or less for up to seven days at ambient temperatures or, at a pressure of 0.5 mm of mercury for up to eighteen hours followed by vacuum drying at a temperature of 140° C. for at least four hours. At the end of the drying period, the dried polymer was discharged directly into tared vacuum containers, weighed and stored.

Extrusion/Orientation:

The polymer was extruded in a V100 vertical extruder, with a 1" screw diameter. During this trial, a size one Zenith pump was use to maintain a die at a pressure of approximately 2160 psi. The die size used was a 12 mil 40 hole die with a 7:1 length/diameter capillary ratio. This combination of pressure and die configuration allowed continuous collection of an unoriented 406 denier product. A Leesona winder was used to collect this extrudate at a rate of 1250 feet per minute.

In order to evolve the maximum physical properties of the extrudate yarn, it was necessary to stretch, or orient, the yarn while it was exposed to heat. This was accomplished by leading the fiber around a series of heated rolls turning at different speeds relative to one another. The first roll, or feed roll turned at 133 feet per minute and was heated to a temperature of 210° F. The second roll, or draw roll turned at 732 feet per minute and was heated to a temperature of 295° F. This results in the fiber being stretched to 5.5 times its original length. From the draw roll, which turned at 732 feet per minute, the fiber proceeds to the let off roll, which was at room temperature and turned at a rate of 865 feet per minute. The fiber was stretched a total of 6.5 times its original length. The yarn properties such as denier, tenacity, and elongation were then measured.

Textile Processing

Braided suture may have different braid construction, however, the suture described herein after were Size 2 suture (with similar constructions when compared within a table). The yarn was first twisted on a Hamel 2000 down twister. This machine has the capabilities of single end twisting and plying which suits the needs of this suture preparation. The twist level which was determined by feed roll speed and spindle speed is set at 6 turns per inch (tpi) in two directions, "S" and "Z". This is to counterbalance the torque in the braiding operation. The six turns per inch level is also in the core material which is plied.

The sheath yarns which consist of a single end of 62.5 denier is twisted at the above level. Three ends of 62.5 denier yarn are also twisted or plied together at 6 tpi. The yarn was then taken to the Hacoba bobbin winder for winding onto braider bobbins. Sixteen bobbins will contain the single 62.5 denier material due to the number of carriers on the braiders and four bobbins will contain the plied material which is now known as 62.5/3. Once the yarn was bobbin wound, each single end bobbin was placed on a braider carrier. The braiders were sixteen carrier, New England Butt braiders, with a Maypole configuration. They were manufactured by the Wardwell Machine Company. The 62.5/3 yarn was placed below the braiders and was pulled off parallel to the flange. Tension was monitored on the core so as not to cause potential core popping and bunching. The pick gear which monitors the density of the braid was set at 82/30 which yields approximately 45 picks per inch. The braider runs at approximately 11 yards per hour.

Once the braid is complete, the material was doffed and scoured in isopropyl alcohol for fifteen minutes. It was scoured in skein form and then air dried. The skein was then wound onto a double flanged plastic bobbin which was used as the let off spool for the next operation, hot stretching. The hot stretching, which was a drawing process, was accomplished by moving the braid through a series of heated rollers at subsequently higher speeds. This material was run at 100 feet per minute using a 10 percent draw ratio with the draw rollers at a temperature of 85° C. It was then ready for coating.

Coating

The spool of material was placed on the let off device and the end of the suture was threaded through a coating line. The suture was fed through guide wires and into a coating dip tank. The suture goes over and under a series of rollers which ensures that the suture passes through the coating solution bath. The coating solution was made by adding coating copolymer (90/10 poly($\epsilon$-caprolactone-co-glycolide) initiated with glycolic acid having an inherent viscosity 0.45 dL/g as measured in HFIP at 25° C. at a concentration of 0.1 g/dL) to ethyl acetate solvent. The mixture was then stirred until all of the copolymer is in solution. The coating bath was filled with the solution. The coating unit was exhausted to remove excess solvent vapors. The suture then travels single pass through the drying tunnel, 16 feet long at a temperature of 120° F. at a speed of 80 meters/minute.

Annealing

The suture was then rack wound under tension and annealed in a Blue M oven for 10 hours at 80° C. At the end of that time, the suture was unwound and spooled.

The characteristic properties of the sutures of the invention were determined by conventional test procedures. The tensile properties (i.e., straight and knot tensile strengths and elongation) displayed herein were determined with an INSTRON Tensile Tester. The settings used to determine the straight tensile, knot tensile and break elongation were the following, unless indicated:

TABLE 2

|  | GAUGE LENGTH (cm) | CHART SPEED (cm) | CROSSHEADSPEED (cm/ min.) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength was calculated by dividing the force to break by the initial cross-sectional area of the suture. The elongation at break was read directly from the stress-strain curve of the sample.

The knot tensile strength of a suture was determined in separate tests. A simple knot (single throw—right over left) by forming a loop in the left hand. The right end was passed behind the left end and pulled forward through the center of the loop with the right hand was tied (see FIGURE). The strand is placed in the Instron jaws so that the knot is created approximately midway between the grips.

The specimen was placed in the INSTRON Tensile Tester with the knot approximately midway between the clamps. The knot tensile strength was calculated by dividing the force required to break by the initial cross-sectional area of the fiber. The tensile strength values are reported in KPSI (i.e. 1,000 psi).

The physical data for this spool is as follows:

| Diameter (mils) | Straight Tensile (lbs) | Percent Elongation | Knot Tensile (lbs) |
|---|---|---|---|
| 24.36 | 29.12 | 32.0 | 15.90 |

EXAMPLE 2

This Example provides a comparison of the inventive suture described in Example 1 and a suture prepared using a conventional process. Conventionally processed sutures where prepared by annealing the suture before coating the suture using the same processing conditions as described in Example 1. The braided sutures were then tested.

The following table outlines three lots of suture material that were processed under both the standard process flow, anneal/coat and the new process flow coat/anneal. In each lot there was a significant increase in knot tensile strength when the new process was used.

| Sample Number | Knot Strength Annealed/Coated (lbs.) | Knot Strength Coated/Annealed (lbs.) |
|---|---|---|
| Sample 1 | 14.93 | 15.95 |
| Sample 2 | 14.15 | 15.56 |
| Sample 3 | 14.77 | 15.90 |

The process of annealing after coating was also evaluated on different size braided structures. The braided material was processed in the traditional manner up to annealing. The material was coated first and then annealed. Another set of material was annealed prior to coating and then subjected to a post coating heat treatment. Both of these materials were tested, as described in Example 1, and compared to material processed in the traditional process flow. In both cases of the coating material being distributed into the braid due to post coating heat exposure (coating-anneal, and anneal-coating-heat treat), the tensile properties were increased compared to tensile properties of the traditional process flow. The data is summarized in the tables below and it can be seen that although some increase are less than 1% the trend is always that redistributing the coating increases the tensile strength.

| Size | Treatment | Straight Average | Straight SD | Straight % Change from A/C | Knot Average | Knot SD | Knot % Change from A/C |
|---|---|---|---|---|---|---|---|
| 2 | Traditional-Anneal/Coated | 38.86 | 0.81 | 0.00% | 25.95 | 1.17 | 0.00% |
| 2 | Coated Annealed | 39.71 | 0.84 | 2.19% | 26.11 | 0.55 | 0.62% |
| 2 | Annealed/Coated/Heat Treat | 39.88 | 0.72 | 2.62% | 26.07 | 0.66 | 0.46% |
| 0 | Traditional-Anneal/Coated | 24.26 | 0.31 | 0.00% | 13.53 | 0.58 | 0.00% |
| 0 | Coated Annealed | 24.35 | 0.46 | 0.37% | 14.26 | 0.42 | 5.40% |
| 0 | Annealed/Coated/Heat Treat | 24.34 | 0.38 | 0.33% | 14.55 | 0.37 | 7.54% |
| 3/0 | Traditional-Anneal/Coated | 10.16 | 0.40 | 0.00% | 6.22 | 0.35 | 0.00% |
| 3/0 | Coated Annealed | 10.47 | 0.39 | 3.05% | 6.50 | 0.24 | 4.50% |
| 3/0 | Annealed/Coated/Heat Treat | 10.52 | 0.26 | 3.54% | 6.58 | 0.25 | 5.79% |

We claim:

1. A process for producing a braided suture having an improved knot strength comprising coating a braided suture with a biocompatible polymer to produce a coated braided suture and heating the coated braided suture to a temperature sufficient to allow the biocompatible polymer to flow for a time ranging a from 20 minutes to 72 hours to allow the polymer to be redistributed into the interstices of the braided suture thereby providing a coated braided suture with an improved knot tensile strength.

2. The process of claim 1 wherein the biocompatible polymer is a low molecular weight biocompatible polymer selected from the group consisting of aliphatic polyesters, polyoxalates, polyoxaesters and combinations thereof.

3. The process of claim 1 wherein the braided sutures is absorbable.

4. The process of claim wherein the absorbable suture is a homopolymer or copolymer of a monomer selected from the group consisting of glycolide, lactide, 1,4-dioxan-2-one, trimethylene carlionate, δ-valerolactone, ε-caprolactone, 1,4-dioxepan-2-one, 1,5-dioxepan-2-one, alkyl substituted derivatives of these compounds, cyclic dimers of these compounds and combinations of two or more thereof.

5. The process of claim 4 wherein the braided suture is a copolymer of glycolide and lactide.

6. The braided suture of claim 4 wherein the braided suture is a copolymer of ε-caprolactone and glycolide.

7. The process of claim 4, wherein the braided suture is a copolymer containing trimethylene carbonate and at least one other lactone monomer.

8. The process of claim 1, wherein the biocompatible polymer is a copolymer of ε-caprolactone and glycolide.

9. The process of claim 1, wherein the temperature to which the biocompatible polymer is heated is above 60° C.

10. The process of claim 9, wherein the temperature to which the biocompatible polymer is heated is less than 100° C. above the softening temperature of the biocompatible polymer.

11. The process of claim 1, wherein the coated braided suture heated for about 30 minutes to about 72 hours.

* * * * *

UNITED STATES PATENT AND TRADEMARK OFFICE
CERTIFICATE OF CORRECTION

PATENT NO. : 6,712,838 B2
DATED : March 30, 2004
INVENTOR(S) : D'Aversa et al.

It is certified that error appears in the above-identified patent and that said Letters Patent is hereby corrected as shown below:

<u>Column 10,</u>
Line 52, delete "a".
Line 62, after the word claim insert -- 3 --.
Line 66, "carlionate" should read -- carbonate --.

<u>Column 12,</u>
Line 9, after the word suture insert -- is --.

Signed and Sealed this

First Day of June, 2004

JON W. DUDAS
*Acting Director of the United States Patent and Trademark Office*